(12) United States Patent
Christenson et al.

(10) Patent No.: US 11,391,709 B2
(45) Date of Patent: Jul. 19, 2022

(54) ISOLATED SENSOR AND METHOD OF ISOLATING A SENSOR

(71) Applicant: Carrier Corporation, Palm Beach Gardens, FL (US)

(72) Inventors: John Carl Christenson, Prior Lake, MN (US); David P. Potasek, Lakeville, MN (US); Roger Alan Backman, Minneapolis, MN (US)

(73) Assignee: CARRIER CORPORATION, Palm Beach Gardens, FL (US)

( * ) Notice: Subject to any disclaimer, the term of this patent is extended or adjusted under 35 U.S.C. 154(b) by 178 days.

(21) Appl. No.: 16/325,874

(22) PCT Filed: Aug. 18, 2017

(86) PCT No.: PCT/US2017/047626
§ 371 (c)(1),
(2) Date: Feb. 15, 2019

(87) PCT Pub. No.: WO2018/035468
PCT Pub. Date: Feb. 22, 2018

(65) Prior Publication Data
US 2019/0212313 A1 Jul. 11, 2019

Related U.S. Application Data

(60) Provisional application No. 62/376,811, filed on Aug. 18, 2016.

(51) Int. Cl.
*G01N 33/00* (2006.01)

(52) U.S. Cl.
CPC ..... *G01N 33/0031* (2013.01); *G01N 33/0027* (2013.01)

(58) Field of Classification Search
CPC .................. G01N 33/0027; G01N 33/0031
See application file for complete search history.

(56) References Cited

U.S. PATENT DOCUMENTS

| 5,907,765 | A | 5/1999 | Lescouzeres et al. |
| 6,071,476 | A | 6/2000 | Young et al. |
| 6,111,280 | A | 8/2000 | Gardner et al. |
| 6,137,708 | A | 10/2000 | Lin et al. |
| 6,763,699 | B1 | 7/2004 | Hunter et al. |
| 6,997,040 | B1 | 2/2006 | Lee et al. |

(Continued)

FOREIGN PATENT DOCUMENTS

| CN | 101762623 A | 6/2010 |
| CN | 102778479 A | 11/2012 |

(Continued)

OTHER PUBLICATIONS

Briand, Danick, "Thermallly Isolated Microelectronic Devices for Gas Sensing Applications", Institute of Microtechnology, University of Neuchatel, 2001, 280 pages.

(Continued)

*Primary Examiner* — Justin N Olamit
(74) *Attorney, Agent, or Firm* — Cantor Colburn LLP

(57) ABSTRACT

An isolated sensor and method of isolating a sensor are provided. The isolated sensor includes a mounting portion, a sensor portion disposed adjacent to the mounting portion, and at least one pedestal connecting a mounting portion to a sensor portion.

4 Claims, 7 Drawing Sheets

(56) References Cited

U.S. PATENT DOCUMENTS

| | | |
|---|---|---|
| 7,368,769 B2 | 5/2008 | Paik |
| 7,389,672 B2 | 6/2008 | Howard et al. |
| 7,495,300 B2 | 2/2009 | Gardner et al. |
| 7,628,907 B2 | 12/2009 | Gu et al. |
| 7,849,727 B2 | 12/2010 | Gardener et al. |
| 8,293,556 B2 | 10/2012 | Park et al. |
| 8,534,117 B2 | 9/2013 | Jones et al. |
| 9,343,367 B2* | 5/2016 | Goida ................... H01L 23/562 |
| 10,180,406 B2* | 1/2019 | Biancolillo ............... B81B 7/02 |
| 2014/0260545 A1 | 9/2014 | Ruhl et al. |
| 2015/0021716 A1 | 1/2015 | Lee et al. |
| 2015/0160145 A1 | 6/2015 | Feyh et al. |
| 2015/0362451 A1 | 12/2015 | Hunziker et al. |
| 2016/0033436 A1 | 2/2016 | Matsukura et al. |
| 2016/0103082 A1 | 4/2016 | Kimura |
| 2017/0029270 A1 | 2/2017 | Potasek et al. |
| 2017/0097314 A1 | 4/2017 | Christenson et al. |

FOREIGN PATENT DOCUMENTS

| | | | |
|---|---|---|---|
| CN | 104617095 A | 5/2015 | |
| CN | 104627947 A | 5/2015 | |
| CN | 105116023 A | 12/2015 | |
| EP | 0822578 A1 | 10/2003 | |
| EP | 1886127 B1 * | 5/2012 | ........... G01N 27/128 |
| EP | 1886127 B1 | 5/2012 | |
| EP | 2952886 A1 | 12/2015 | |
| WO | 2007025100 A2 | 3/2007 | |

OTHER PUBLICATIONS

International Search Report and Written Opinion for application PCT/US2017/047626, dated Nov. 7, 2017, 11 pages.

* cited by examiner

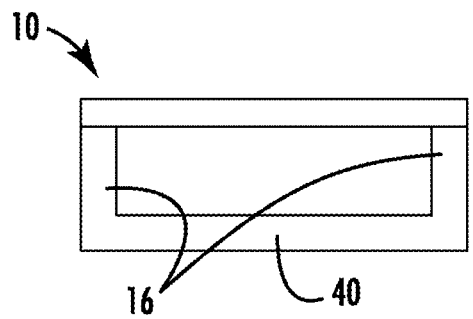
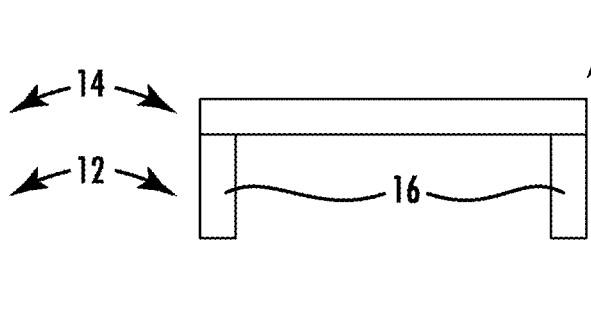
FIG. 5A  FIG. 5B
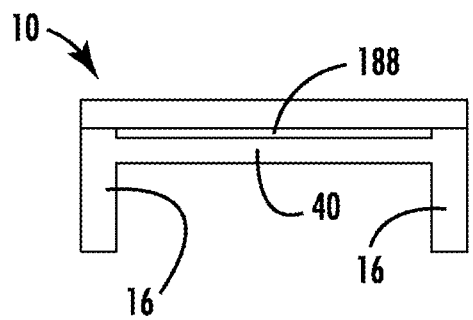
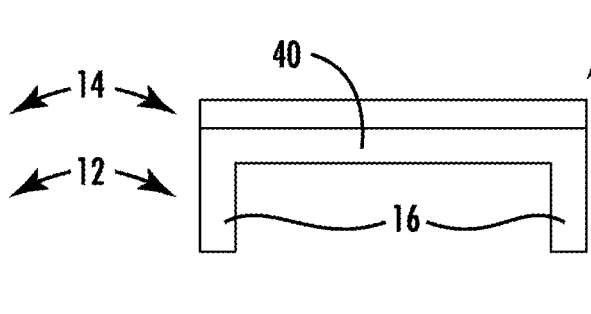
FIG. 5C  FIG. 5D
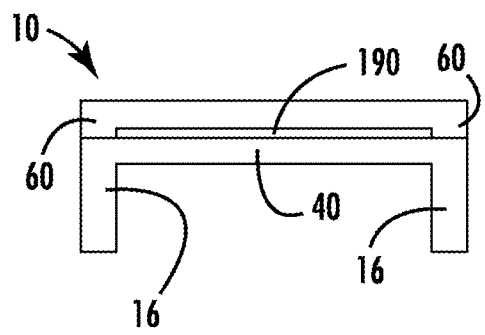
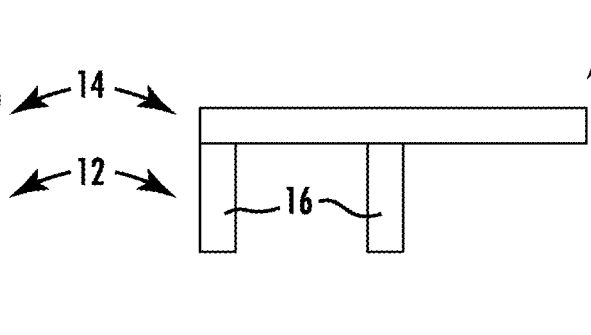
FIG. 5E  FIG. 5F
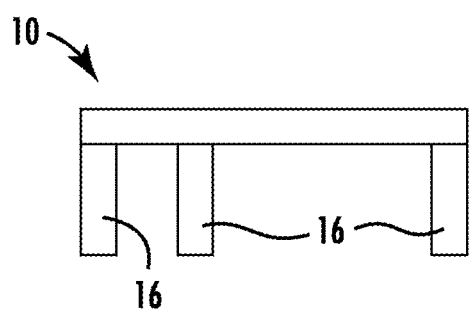
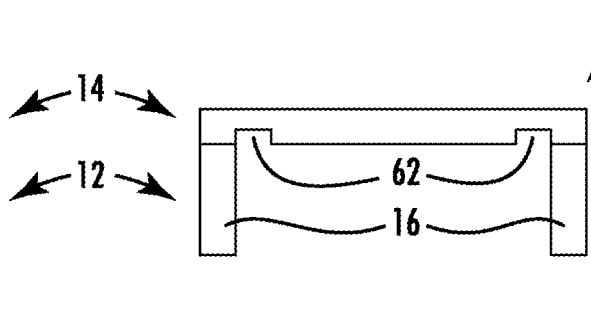
FIG. 5G  FIG. 5H

ISOLATED SENSOR AND METHOD OF ISOLATING A SENSOR

CROSS REFERENCE TO RELATED APPLICATION

The present application is an international application, which claims the priority benefit of U.S. Patent Application 62/376,811, filed Aug. 18, 2016, which is herein incorporated in its entirety.

TECHNICAL FIELD OF THE DISCLOSED EMBODIMENTS

The presently disclosed embodiments generally relate to a sensor and a method of manufacturing a sensor. More particularly, the embodiments relate to a thermally and stress isolated sensor and a method of thermally and stress isolating a sensor.

BACKGROUND OF THE DISCLOSED EMBODIMENTS

Some sensors, such as metal oxide semiconductor (MOS) gas sensors, require strict temperature control across the sense material for accurate operation. In the case of gas sensors, temperature control assures sensitivity of the sensor to only the target gas. A sensor mounted to a substrate or header, electrical connections or other leads running to the sensor, or other conventional sensor structures may sink heat away from the sensor, thereby decreasing the thermal uniformity of the sensor. Sensors which are operated at relatively high temperatures may be prone to strains in their sensor material due to thermal expansion mismatch between components in the assembly. Further, heat losses to mounting structure or electrical leads increases the power usage of the sensor assembly.

Therefore, there remains a need for a sensor that is thermally and stress isolated from its mounting structure and operates with improved temperature uniformity. Further, there exists a need for a thermally isolated sensor that reduces the power usage requirement of the sensor assembly. Finally, there exists a need for a method of efficiently manufacturing a thermally and stress isolated sensor.

SUMMARY OF THE DISCLOSED EMBODIMENTS

In accordance with an embodiment of present disclosure, an isolated sensor is provided. The isolated sensor includes a mounting portion, a sensor portion disposed adjacent to the mounting portion, and at least one pedestal connecting a mounting portion edge to a sensor portion edge.

The isolated sensor may further include at least one electrical connection disposed upon the sensor portion. The at least one pedestal may include a plurality of pedestals connecting a plurality of mounting portions to a plurality of sensor portions. The plurality of mounting portions and the plurality of sensor portions may include a plurality of mounting portion corners and a plurality of sensor portion corners. The sensor portion may be a gas sensor configured to operate within a temperature range. The mounting portion may be coupled to the sensor portion only by the at least one pedestal. The isolated sensor may further include an isolated at least one planar portion interconnecting at least two pedestals. The isolated sensor may further include at least one insulating gap disposed between the planar portion and the sensor portion.

In accordance with an embodiment of the present disclosure, a method of isolating a sensor is provided. The method includes providing a mounting wafer, providing a sensor wafer having a plurality of sensors, removing a portion of the mounting wafer to form a plurality of mesas, and positioning the sensor wafer on the plurality of mesas such that the plurality of sensors is isolated from the plurality of mesas.

Positioning the sensor wafer on the plurality of mesas may include positioning the sensor wafer such that the plurality of sensors is thermally and stress isolated from the plurality of mesas. Removing the portion of the mounting wafer may include forming a plurality of channels to form the plurality of mesas. The method may further include bonding the sensor wafer to the plurality of mesas. The method may further include singulating each of the plurality of sensors. Singulating each of the plurality of sensors may include forming a plurality of mounting portion edges and a plurality of sensor portion edges. Singulating each of the plurality of sensors may include forming a plurality of mounting portion corners and a plurality of sensor portion corners. Singulating each of the plurality of sensors may include cutting the mounting wafer and the sensor wafer simultaneously through at least one of the plurality of mesas to form an isolated sensor assembly. Singulating each of the plurality of sensors may form a plurality of pedestals. Removing a portion of the mounting wafer may form at least one planar portion interconnecting at least one of the plurality of pedestals. The method may further include forming an insulating gap between the planar portion and the sensor portion. The method may further include bonding at least one electrical connection to the isolated sensor assembly at one of the plurality of pedestals.

BRIEF DESCRIPTION OF THE DRAWINGS

The embodiments and other features, advantages and disclosures contained herein, and the manner of attaining them, will become apparent and the present disclosure will be better understood by reference to the following description of various exemplary embodiments of the present disclosure taken in conjunction with the accompanying drawings, wherein:

FIG. 5A illustrates an isolated sensor assembly according to one embodiment of the present disclosure;

FIG. 5B illustrates an isolated sensor assembly according to one embodiment of the present disclosure;

FIG. 5C illustrates an isolated sensor assembly according to one embodiment of the present disclosure;

FIG. 5D illustrates an isolated sensor assembly according to one embodiment of the present disclosure;

FIG. 5E illustrates an isolated sensor assembly according to one embodiment of the present disclosure;

FIG. 5F illustrates an isolated sensor assembly according to one embodiment of the present disclosure;

FIG. 5G illustrates an isolated sensor assembly according to one embodiment of the present disclosure;

FIG. 5H illustrates an isolated sensor assembly according to one embodiment of the present disclosure;

DETAILED DESCRIPTION OF THE ENCLOSED EMBODIMENTS

Figure 1:
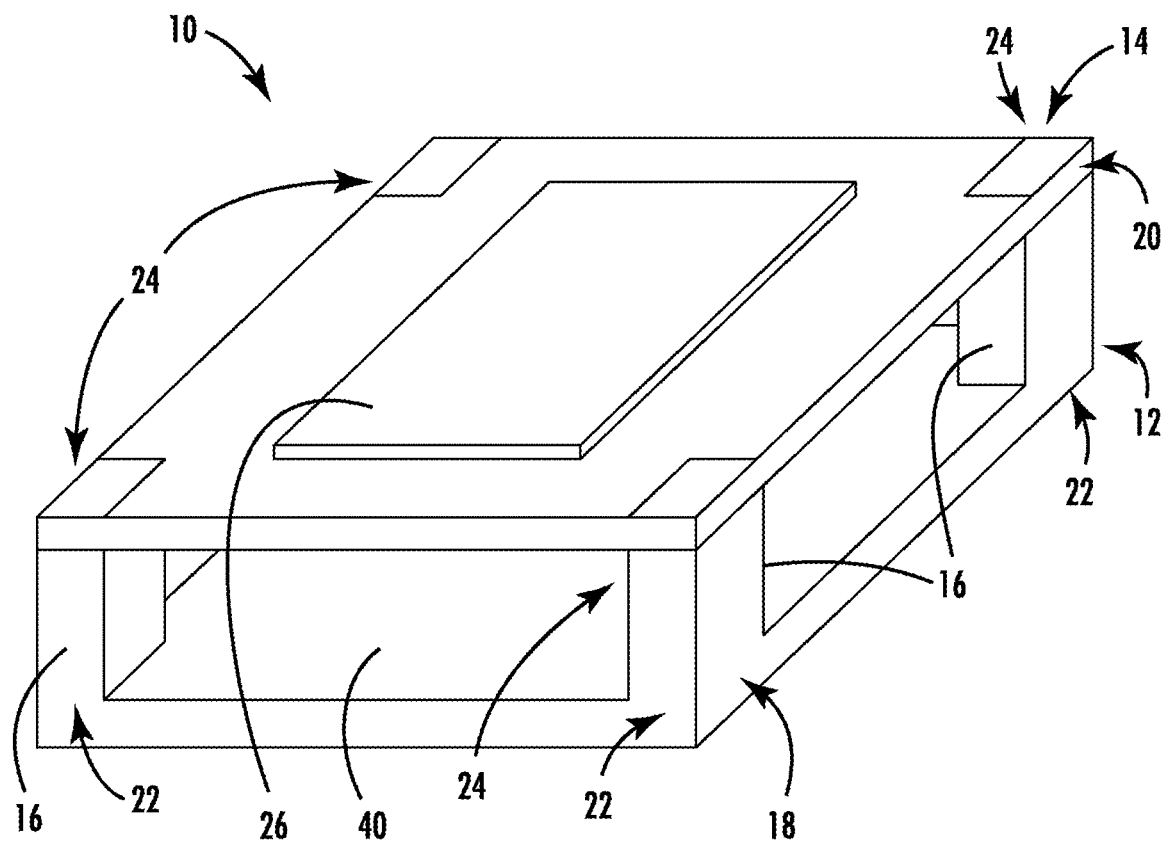
FIG. 1 is a perspective view of an isolated sensor assembly according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Referring now to the drawings, FIG. 1 illustrates an isolated sensor assembly 10 in accordance with one embodiment. The sensor assembly 10 includes a mounting portion 12 and a sensor portion 14 disposed adjacent to the mounting portion 12. The sensor portion 14 of the illustrated embodiment includes a sensor 26, such as a metal oxide semiconductor (MOS) gas sensor, in one non-limiting example, that operates within a predetermined elevated temperature range. Such an elevated temperature range may be between 100 and 350 degrees centigrade in one embodiment. In an embodiment, the temperature range may be greater than 350 degrees or less than 100 degrees centigrade. In another embodiment, the temperature range may be between 150 and 300 degrees centigrade. One of ordinary skill in the art will recognize the various sensors that may be incorporated as the sensor 26 into the sensor portion 14, and such sensors form part of the embodiments of the present disclosure. The present disclosure includes sensor portion 14 being constructed of a single substrate material or of two or more materials, such as two or more layers of substrate materials in non-limiting examples.

The mounting portion 12 of the sensor assembly 10 further includes one or more pedestals 16 connecting a mounting portion edge 18 to a sensor portion edge 20. In the embodiment of FIG. 1, a plurality of pedestals 16 connect a plurality of mounting portion edges 18 to a plurality of sensor portion edges 20. More particularly, in the embodiment, the plurality of pedestals 16 connects a plurality of mounting portion corners 22 to a plurality of sensor portion corners 24. The mounting portion 12 includes a planar portion 40 connecting one or more pedestals 16 in the embodiment. As further illustrated in the non-limiting embodiments of FIGS. 5A to 5H and described below, the number and arrangement of pedestals 16 and the arrangement and structure of the mounting portion 12 and the sensor portion 14 is not limited to the embodiment shown in FIG. 1.

In one embodiment, the mounting portion 12 is coupled to the sensor portion 14 only by one or more pedestals 16. Such an arrangement thermally isolates the sensor 26 from the mounting portion 12 by minimizing the physical structure and conduction area, or maximizing the thermal resistance, connecting the sensor 26 to any exterior structure that may operate as a heat sink. Additionally, such an arrangement stress-isolates the sensor 26 from the mounting portion 12 as well as the header (not shown) to which the sensor assembly 10 is mounted in one embodiment. Further, such an arrangement stress-isolates the method and materials of attachment of the sensor assembly 10 to a header. The thermal isolation results in an improved uniformity in temperature across the sensor 26 due to a reduced opportunity for heat to escape to the surrounding structure. With reduced heat loss, energy efficiency of the sensor assembly 10 is improved as less energy is required to maintain the required operating temperature of the sensor 26. The stress isolation prevents strains in the sensor 26. Strains in the sensor 26 may disadvantageously change the output of the sensor 26 relative to a non-strained sensor 26 that experiences the same environmental conditions.

Figure 2:
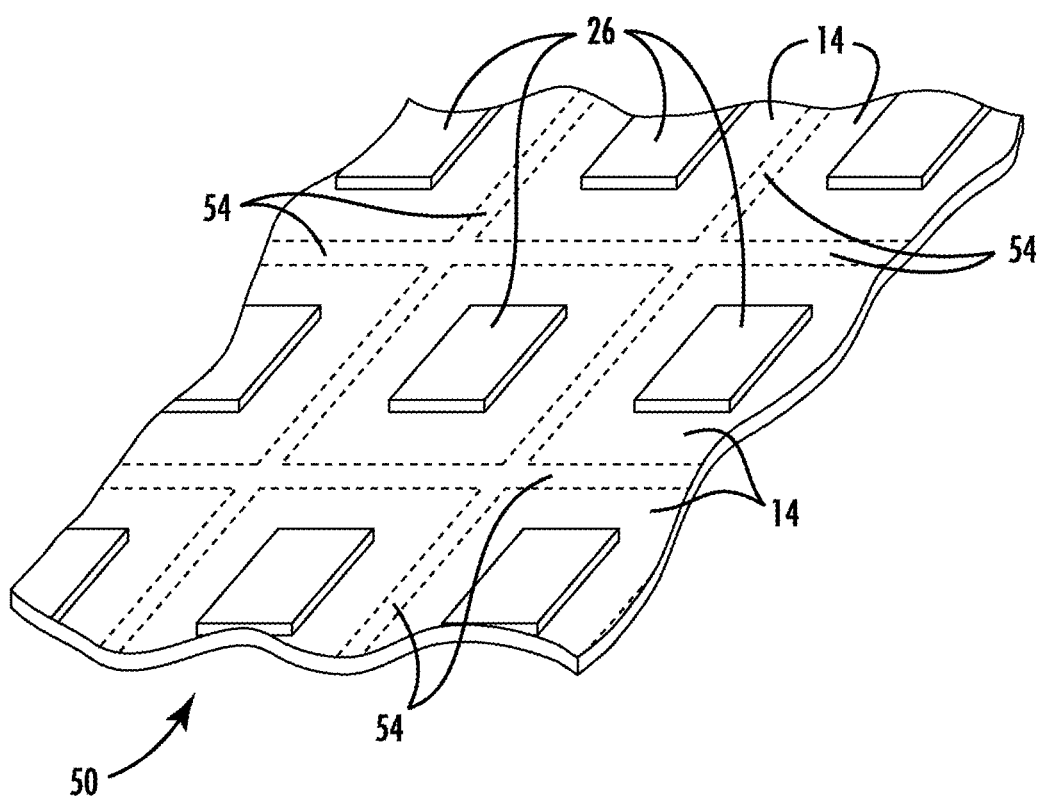
FIG. 2 is a perspective view of a portion of a sensor wafer according to one embodiment of the present disclosure.
Figure 3:
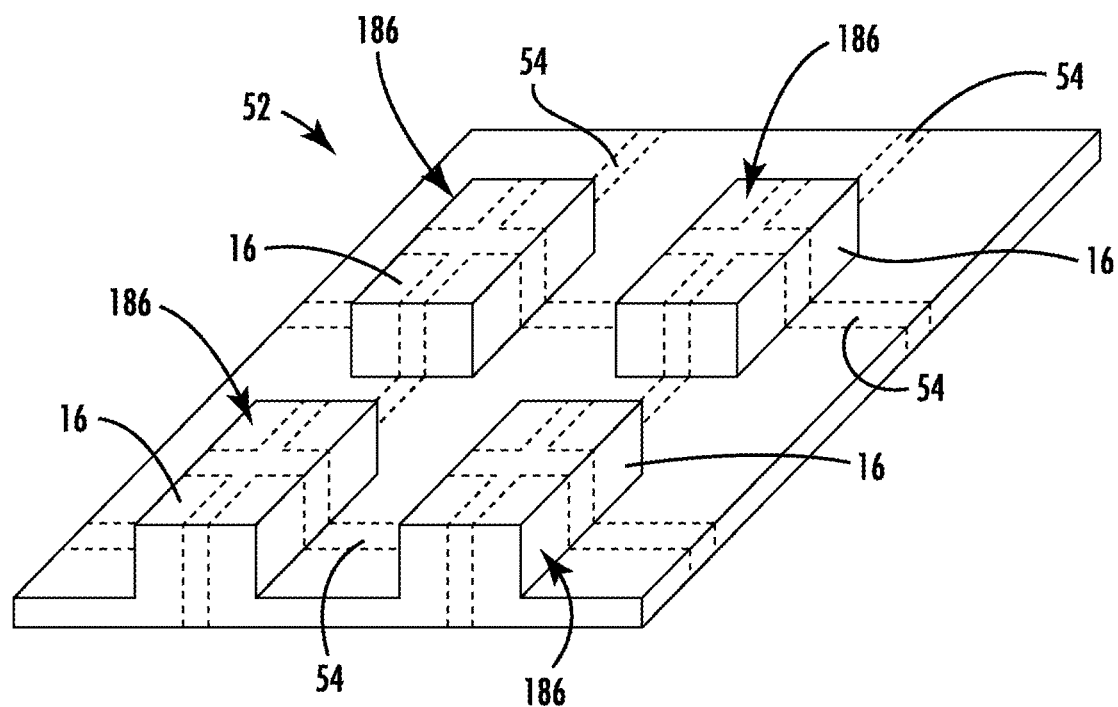
FIG. 3 is a perspective view of a portion of a mounting wafer according to one embodiment of the present disclosure.

Referring now to FIGS. 2 and 3, the sensor assembly 10 is initially formed from a sensor wafer 50 having a plurality of sensors 26 and sensor portions 14, as illustrated in FIG. 2, and a mounting wafer 52 having a plurality of mesas 186, as illustrated in FIG. 3. As will be explained in further detail below, multiple sensor assemblies 10 of one embodiment are formed by joining the sensor wafer 50 to the mounting wafer 52 before both wafers 50, 52 are cut or separated along separation lines 54 illustrated in FIGS. 2 and 3.

Figure 4:
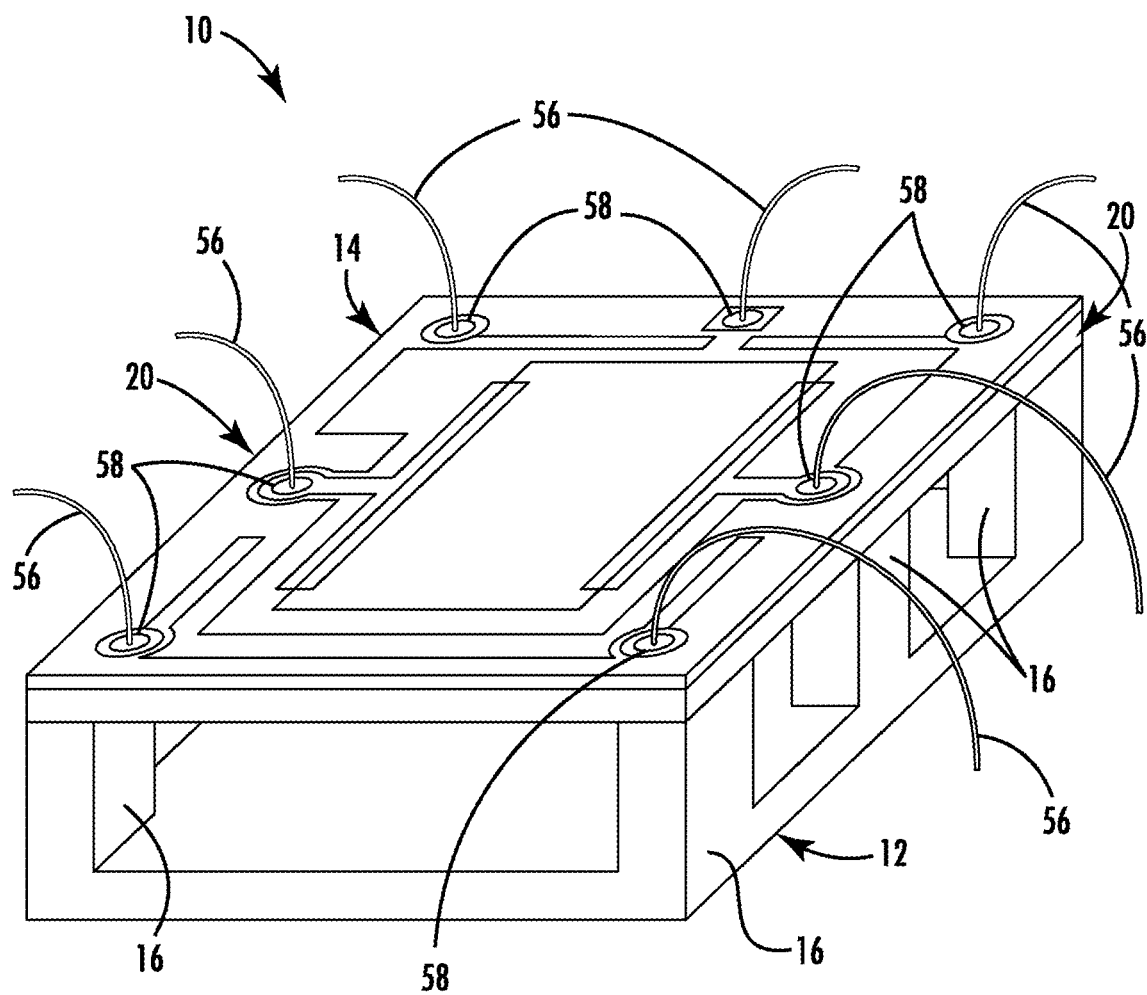
FIG. 4 is a perspective view of an isolated sensor assembly according to one embodiment of the present disclosure.

In the embodiment illustrated in FIG. 4, the sensor assembly 10 includes one or more electrical connections 56, such as wires in one non-limiting example, bonded to the sensor portion 14 as known by one having ordinary skill in the art. The electrical connections 56 are disposed at the sensor portion edge 20 in the illustrated embodiment. The coupling point 58 of the electrical connections 56 acts as a point of heat loss, as previously described. In the embodiment, one or more electrical connections 56 are positioned adjacent to one or more pedestals 16. In an embodiment, one or more electrical connections 56 is aligned with the pedestal 16 such that the coupling point 58 is supported by the pedestal 16 and/or is not cantilevered on the sensor portion 14. In one embodiment, one or more pedestals 16 provide physical support for installation, bonding, or otherwise coupling one or more electrical connections 56 to the sensor portion 14. In one or more additional embodiments, the coupling points 58 and/or pedestals 16 are not positioned at the circumference or edges 20 as illustrated in FIG. 4. Non-limiting examples of embodiments, including one or more of the embodiments illustrated in FIGS. 5A-5H, have one or more non-circumferential or non-edge coupling points 58 and/or pedestals 16 arrangements.

Referring now to FIGS. 5A through 5H, several non-limiting embodiments of the sensor assembly 10 are illustrated. FIG. 5A illustrates the sensor assembly 10 having the arrangement of FIG. 1. The planar portion 40 allows for a means of connecting pedestals 16 to one another, resulting in improved structural stability of pedestals 16, as well as allowing an intimate and large contact area of a bottom surface of planar portion 40 to a sensor mounting (not shown). FIG. 5B illustrates the sensor assembly 10 having the mounting portion 12 without the planar portion 40 connecting the plurality of pedestals 16. The embodiment of FIG. 5B does not include the planar portion 40 of FIG. 5A, but allows for minimal contact of the sensor assembly 10 to a sensor mounting. FIG. 5C illustrates the sensor assembly 10 having the planar portion 40 disposed at a central location of the plurality of pedestals 16 with an insulating gap 188 between the planar portion 40 and the sensor portion 14. FIG. 5C further illustrates the sensor assembly 10 having advantageous features of embodiments illustrated in FIGS. 5A and 5B, including the structural stability of interconnected pedestals 16 afforded by planar portion 40 and the minimal contact area of the sensor assembly 10 to a sensor mounting. FIG. 5D illustrates the sensor assembly 10 having the planar portion 40 disposed at an upper location of the plurality of pedestals 16. The embodiment of FIG. 5D allows an intimate and large contact area of a top surface of the planar portion 40 to a bottom surface of the sensor portion 14 and minimal contact of the sensor assembly 10 to a sensor mounting. FIG. 5E illustrates the sensor assembly 10 having the planar portion 40 disposed at an upper location of the plurality of pedestals 16 and a sensor portion 14 having a plurality of sensor pedestals 60 coupled to an upper surface of the mounting portion 12 to form an insulating gap 190 between the planar portion 40 and the sensor portion 14. FIG. 5F illustrates the sensor assembly 10 having the mounting portion 12 without the planar portion 40 connecting the plurality of pedestals 16 that are not all disposed at an edge or corner of the sensor portion 14, allowing for cantilevered structures in one or more embodiments. FIG. 5G similarly illustrates the sensor assembly 10 having the mounting portion 12 without the planar portion 40 connecting the plurality of pedestals 16 that are disposed at the edges of the sensor portion 14 as well as a central portion of the sensor portion 14, allowing for internal, non-circumferential, and/or asymmetric arrangements of pedestals 16 in one or more embodiments. FIG. 5H illustrates the sensor assembly 10 having the mounting portion 12 without the planar portion 40 connecting the plurality of pedestals 16 and the sensor portion 14 having at least stress and thermally isolating channels 62 disposed on a lower surface of the sensor portion 14. The embodiments of the present disclosure include any arrangement, geometry, orientation, and dimensions of mesas 186, pedestals 16, and planar portions 40, as well as contact areas between mounting portions 12 and sensor portions 14.

Figure 6:
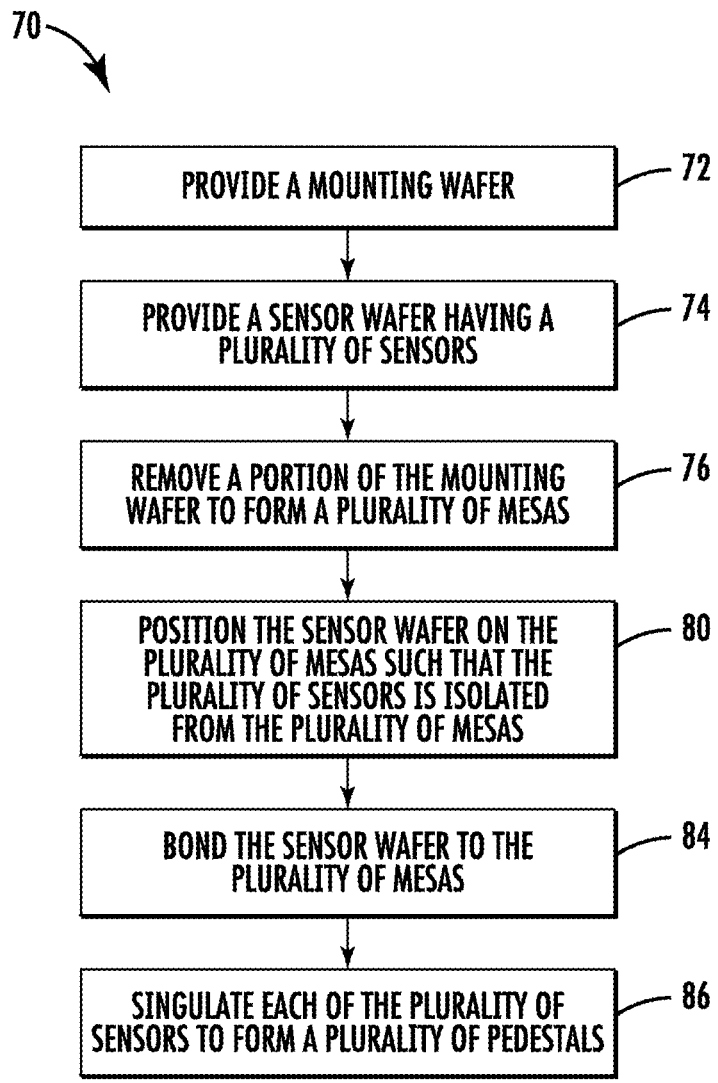
FIG. 6 is a process flow diagram that illustrates a method of isolating a sensor according to one embodiment of the present disclosure.

Referring now to FIG. 6, a method 70 of isolating the sensor 26 is provided. The method 70 includes providing, at step 72, the mounting wafer 52 and providing, at step 74, a sensor wafer 50 having a plurality of sensors 26.

Figure 7:
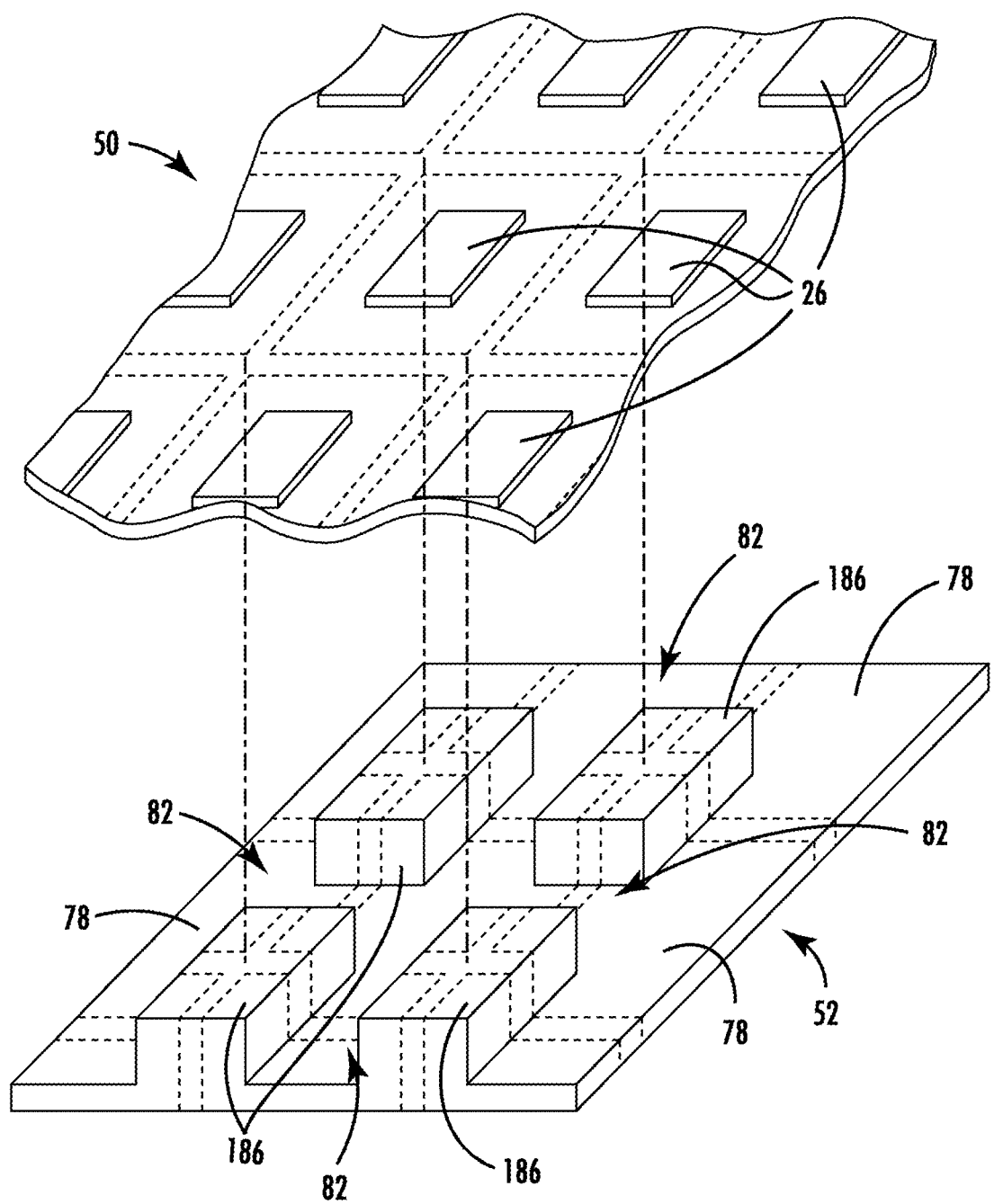
FIG. 7 illustrates a method of isolating a sensor according to one embodiment of the present disclosure.

The method 70 further includes removing, at step 76, a portion 78 of the mounting wafer 52 to form a plurality of mesas 186. With reference to FIG. 7, the portion 78 removed from the mounting wafer 52 of one embodiment includes a plurality of channels 82 in a grid pattern. Removal of the portion 78 may be accomplished by machining, planing, sawing, etching, or any other method known to a person having ordinary skill in the art. Although the mesas 186 illustrated in the embodiments are rectangular, the mesas 186 of further embodiments may have any geometry, including a circular, triangular, hexagonal, or square profile or shape. In a further embodiment, the method 70 does not include removal of the portion 78 and includes coupling the mesas 186 to a planar portion of the mounting wafer 52 to form the mounting wafer 52.

As best illustrated in FIG. 7, the method 70 further includes positioning, at step 80, the sensor wafer 50 on the plurality of mesas 186 such that the plurality of sensors 26 is isolated from the plurality of mesas 186. In one embodiment, the method 70 further includes bonding, at step 84, the sensor wafer 50 to the plurality of mesas 186. In additional embodiments, the sensor wafer 50 is fastened, adhered, fused, or otherwise coupled to the plurality of mesas 186 in accordance with any method known to a person having ordinary skill in the art.

The method 70 further includes singulating, at step 86, each of the plurality of sensors 26. In an embodiment, the method 70 includes singulating, at step 86, each of the plurality of sensors 26 to form the plurality of pedestals 16. In additional embodiments, the sensor wafer 50 is cut, sawed, or otherwise separated into multiple pieces in accordance with methods known to a person of ordinary skill in the art. In one embodiment, singulating or separating each of the plurality of sensors 26 includes cutting the mounting wafer 52 and the sensor wafer 50 simultaneously through the plurality of mesas 186 to form the isolated sensor assembly 10. In an embodiment, such as the embodiment illustrated in FIG. 1, the singulation step 86 forms the one or more mounting portion edges 18, the one or more sensor portion edges 20, the one or more mounting portion corners 22, and the one or more sensor portion corners 24. Additionally, the singulation step 86 forms the one or more pedestals 16 from the mesas 186 in one or more embodiments. The singulation or separation into the individual sensor assemblies 10 involves cutting, sawing, cleaving, or otherwise separating along the separation lines 54. The method 70 of one embodiment further includes bonding or otherwise coupling at least one electrical connection 56 to the sensor assembly 10 at one of the plurality of pedestals 16. The bonding may include wire bonding, fastening, adhering, fusing, or other methods known to a person having ordinary skill in the art.

It will be appreciated that the embodiments provided in the present disclosure thermally and stress isolate the sensor 26 from mounting structure, such as the mounting portion 12, by minimizing the physical structure connecting the sensor 26 to such a structure acting as a heat sink. The thermal isolation results in an improved uniformity in temperature across the sensor 26 due to a reduced opportunity for heat to escape to surrounding structure. With reduced heat loss, energy efficiency of the sensor assembly 10 is improved as less energy is required to maintain the required operating temperature of the sensor 26. With regard to the method 70, it will be appreciated that the embodiments provided in the present disclosure provide efficient manufacture of multiple sensor assemblies 10 at least partially due to removal of the need to assemble individual portions of each sensor assembly 10.

It will further be appreciated that the embodiments provided in the present disclosure stress-isolate the sensor 26 from a mounting structure, such as the mounting portion 12, by optimizing the physical structure connecting the sensor 26 to such a structure acting as a stress isolator. It will further be appreciated that the embodiments provided in the present disclosure stress-isolate the sensor 26 from a mounting structure by minimizing or mitigating the stress-inducing effects of the mounting, materials, attachment methods and/or materials, and/or structures used in mounting the sensor 26 to a structure, such as a mounting structure and/or a header in two non-limiting examples.

While the disclosure has been illustrated and described in detail in the drawings and foregoing description, the same is to be considered as illustrative and not restrictive in character, it being understood that only certain embodiments have been shown and described and that all changes and modifications that come within the spirit of the disclosure are desired to be protected.

What is claimed is:

1. An isolated sensor, comprising:
   a mounting portion;
   a sensor portion disposed adjacent to the mounting portion;
   at least one pedestal connecting a mounting portion to a sensor portion;
   at least one coupling point on the sensor portion;
   at least one electrical connection connected to the at least one coupling point, the at least one electrical connection coupled to the sensor portion;
   wherein the at least one electrical connection is separate from the at least one pedestal;

at least one planar portion interconnecting at least two pedestals of the at least one pedestal, wherein the at least two pedestals each include a lower portion and an upper portion, the upper portion closer to the sensor portion than the lower portion;

wherein the at least one planar portion interconnects the upper portions of the at least two pedestals;

at least one insulating gap disposed between the planar portion and the sensor portion.

2. The sensor of claim 1, wherein the sensor portion is a gas sensor configured to operate within a temperature range.

3. The sensor of claim 1, wherein the mounting portion is coupled to the sensor portion only by the at least one pedestal.

4. The sensor of claim 1, wherein the at least one electrical connection comprises a wire.

* * * * *